(12) United States Patent
Salmon et al.

(10) Patent No.: US 7,156,818 B2
(45) Date of Patent: Jan. 2, 2007

(54) MULTI-FUNCTIONAL JOINT BRACE

(75) Inventors: Scott Salmon, Hoboken, NJ (US); Dan Ueda, Cliffside Park, NJ (US); Robert Joachim, Glen Rock, NJ (US); Mario Turchi, Tenafly, NJ (US); David C. Hargrave, Madison, NJ (US); Bernard Morrey, Rochester, MN (US); Shawn O'Driscoll, Rochester, MN (US); Robert Adams, Sargent, MN (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 10/357,990

(22) Filed: Feb. 4, 2003

(65) Prior Publication Data
US 2004/0153016 A1 Aug. 5, 2004

(51) Int. Cl.
*A61F 5/00* (2006.01)
(52) U.S. Cl. ............................... 602/5; 602/16; 602/26
(58) Field of Classification Search .................... 602/5, 602/16, 23, 26, 61–63, 27; 128/882
See application file for complete search history.

(56) References Cited

U.S. PATENT DOCUMENTS

| | | | |
|---|---|---|---|
| 3,898,709 A | * | 8/1975 | Lewis et al. ............... 16/329 |
| 4,481,941 A | | 11/1984 | Rolfes |
| 4,531,515 A | | 7/1985 | Rolfes |
| 5,063,916 A | * | 11/1991 | France et al. .............. 602/26 |
| 5,399,154 A | | 3/1995 | Kipnis et al. |
| 5,415,625 A | * | 5/1995 | Cassford et al. ........... 602/26 |
| 5,421,810 A | | 6/1995 | Davis et al. |
| 5,437,619 A | | 8/1995 | Malewicz et al. |
| 5,460,599 A | | 10/1995 | Davis et al. |
| 5,505,668 A | | 4/1996 | Koriakov-Savoysky et al. |
| 5,885,235 A | | 3/1999 | Opahle et al. |
| 5,921,946 A | | 7/1999 | Tillinghast et al. |
| 5,938,629 A | | 8/1999 | Bloedau |
| 5,954,677 A | | 9/1999 | Albrecht et al. |
| 6,039,709 A | * | 3/2000 | Bzoch ........................ 602/26 |
| 6,375,632 B1 | | 4/2002 | Albrecht et al. |

FOREIGN PATENT DOCUMENTS

| | | |
|---|---|---|
| DE | 19606092 | 8/1997 |
| EP | 0841044 A1 | 5/1998 |
| EP | 0841044 B1 | 5/1998 |
| GB | 2326 098 A * | 6/1997 |

* cited by examiner

*Primary Examiner*—Michael A. Brown
(74) *Attorney, Agent, or Firm*—Fish & Neave IP Group, Ropes & Gray LLP (57) ABSTRACT

A multi-functional brace for a joint includes a releasable locking mechanism that allows the brace to be set for static stretch of the joint in either flexion or extension, and a range of motion assembly that allows for free movement of the joint through its natural axis over a controlled range of motion when the locking mechanism is released.

30 Claims, 10 Drawing Sheets

MULTI-FUNCTIONAL JOINT BRACE

BACKGROUND OF THE INVENTION

1. The Field of the Invention

The present invention relates generally to joint support devices, and in particular, to a multi-functional joint brace that protects the joint from internal and external forces and provides for immobilization, static stretching of the joint alternately in flexion and extension, and free movement of the joint over a controlled range of motion.

2. Description of the Related Art

In the health care field, joint support devices are used to protect and promote healing of damaged joints. A wide variety of externally applied supports and braces are known and used in the field. One variety of devices protects joints by immobilization. These devices also can protect the joint by providing a rigid surface that deflects the energy from an external force. A traditional plaster cast is a joint support device that protects by immobilization and by providing a rigid shell.

Another variety of devices promotes healing of a damaged joint by providing controlled stretching of a joint in either a flexed or extended position. One such type of brace locks the joint in an extended or flexed position, and provides dynamic stretching to the joint by means of a spring that exerts a constant torque against the joint as the joint relaxes into the flexed or extended position. The angle of flexion or extension can be gradually adjusted over a range of angles as a joint heals. Such dynamic stretching devices are shown, for example, in U.S. Pat. Nos. 5,399,154 and 5,437,619.

Another type of device provides static rather than dynamic stretching of a joint in either flexion or extension. The device is set at a predetermined angle of flexion or extension and then locked into position to provide static stretching of the joint, which strengthens the muscles and tendons around the joint, but without the use of springs or other means that provide a constant torque against the joint. The angle of flexion or extension can be gradually adjusted as the joint heals. Such devices are shown, for example, in DE 196 06 092 A1, U.S. Pat. Nos. 5,885,235, 5,938,629, 6,039,709 and 6,375,632.

Yet another variety of device promotes healing of a damaged joint by allowing a joint to move freely along its axis of natural movement, while limiting twisting or torsional movement of the joint outside its axis of natural movement. The free movement along the natural axis of the joint can be limited to a predetermined range of flexion or extension. Free movement along this controlled range of motion can strengthen the tendons and muscles in a damaged joint while preventing the weakened joint from being damaged by twisting or moving outside of its natural axis of movement.

The expense and inconvenience of repairing and rehabilitating a joint is increased if more than one brace must be used during the healing process. For example, a rigid cast might be applied first to a broken joint to immobilize the joint for a period of time. Then, a brace that provides a static flexion stretch of the joint might be required after the rigid cast is removed, and yet another brace that provides a static extension stretch of the joint also might be required. To further rehabilitate a damaged joint, a brace that allows controlled free motion of the joint also might be needed. The use of different braces throughout the rehabilitation process can be inconvenient for both the health-care provider and the patient, and can increase the time and expense required to fully heal a damaged joint. Currently available joint support devices do not combine different rehabilitative features into one device.

It is thus one object of the invention to provide a single joint brace device that performs more than one rehabilitative function on a damaged joint.

It is another object of the invention to provide a lightweight, streamlined joint brace device that is more comfortable than prior art devices.

Many of the currently available joint support devices do not interchange easily between joints on the left and right sides of the body, and do not interchange easily between persons of different sizes. It is therefore still another object of the invention to provide a joint brace device that can be used on a joint on either side of the body, and that can be used on patients of various sizes.

SUMMARY OF THE INVENTION

The present invention overcomes the disadvantages in the prior art by providing a lightweight and streamlined joint brace device that can perform different rehabilitative functions. The joint brace disclosed herein achieves advancements over the prior art because of its unique design. The joint brace contains sturdy uprights that provide stability to the wearer. In a preferred embodiment, straps containing air-cells securely hold the brace in position on the user's body, while distributing pressure evenly over the area of the air-cell to prevent wearer discomfort or injury.

The joint brace described herein comprises a hinged movement arm, a means for allowing controlled free movement through the movement arm hinge about a predetermined range of motion, a hinged drive arm, a means for releasably locking said drive arm hinge at a predetermined angle, and adjustable means for connecting said movement arm to said drive arm such that the hinges thereof are in alignment. The means for allowing controlled free movement through the movement arm hinge can comprise a range of motion assembly associated with the movement arm hinge. The means for releasably locking the drive arm can comprise a novel locking mechanism associated with the drive arm hinge that can be used to immobilize a joint by locking the brace into a fixed position. The novel locking mechanism can be switched easily from a locked to an unlocked position, without any time-consuming procedures involving insertion and/or removal of pins into the brace. In the locked position, the brace can statically stretch the joint in either flexion or extension. The brace comprises an angle-adjustment means that can be adjusted so that the brace achieves the desired angle of flexion or extension. The angle-adjustment mechanism can comprise a detailed scale so that the degree of extension and flexion can be closely monitored. The static stretch feature provides the benefits of stability and protection while preparing the joint for eventual movement.

An advantage of the novel design of the brace is that the locking mechanism can be disengaged while the brace is positioned on a wearer to provide the wearer with free movement of the joint within the natural axis of movement while preventing the joint from moving in a direction outside of the joint's natural axis of movement. The range of motion assembly can be adjusted to set the maximum and minimum angle through which the joint can move in flexion and/or extension. Limiting the maximum and minimum angle of motion ensures that the wearer does not exceed predetermined limits, which could injure the joint. The brace advantageously performs the multiple functions of protection, immobilization, static stretching, and controlled free movement of a joint.

The brace can be adjusted easily to fit either the right or left side of a wearer's body, and to fit a wearer of small or large body size. Further, the novel locking mechanism contains no bulky motors or heavy springs, and in a preferred embodiment the adjustment knob of the locking mechanism easily can be removed and reattached as needed for the comfort of the wearer.

The brace also comprises an override means that prevents damage to the locking mechanism when the brace is subjected to a large external force.

These and other advantages of the present invention will become more fully apparent by examination of the following description of the preferred embodiments and the accompanying drawings.

BRIEF DESCRIPTION OF THE SEVERAL VIEWS OF THE DRAWINGS better understand the invention, a more particular description of the invention will be rendered by reference to the appended drawings. These drawings only provide information concerning typical embodiments of the invention and are not to be considered limiting of its scope. The invention will be described and explained with additional specificity and detail through the use of the accompanying drawings, in which.

DETAILED DESCRIPTION OF A PREFERRED EMBODIMENT OF THE INVENTION

The following detailed description is of an embodiment of the invention wherein the multi-functional brace is adapted for use with an elbow. It is to be understood, however, that the invention is not so limited. For example, those skilled in the art will understand how to adapt the principles of the invention as disclosed herein to create a multi-functional brace for use with a knee or any other joint.

Figure 1:
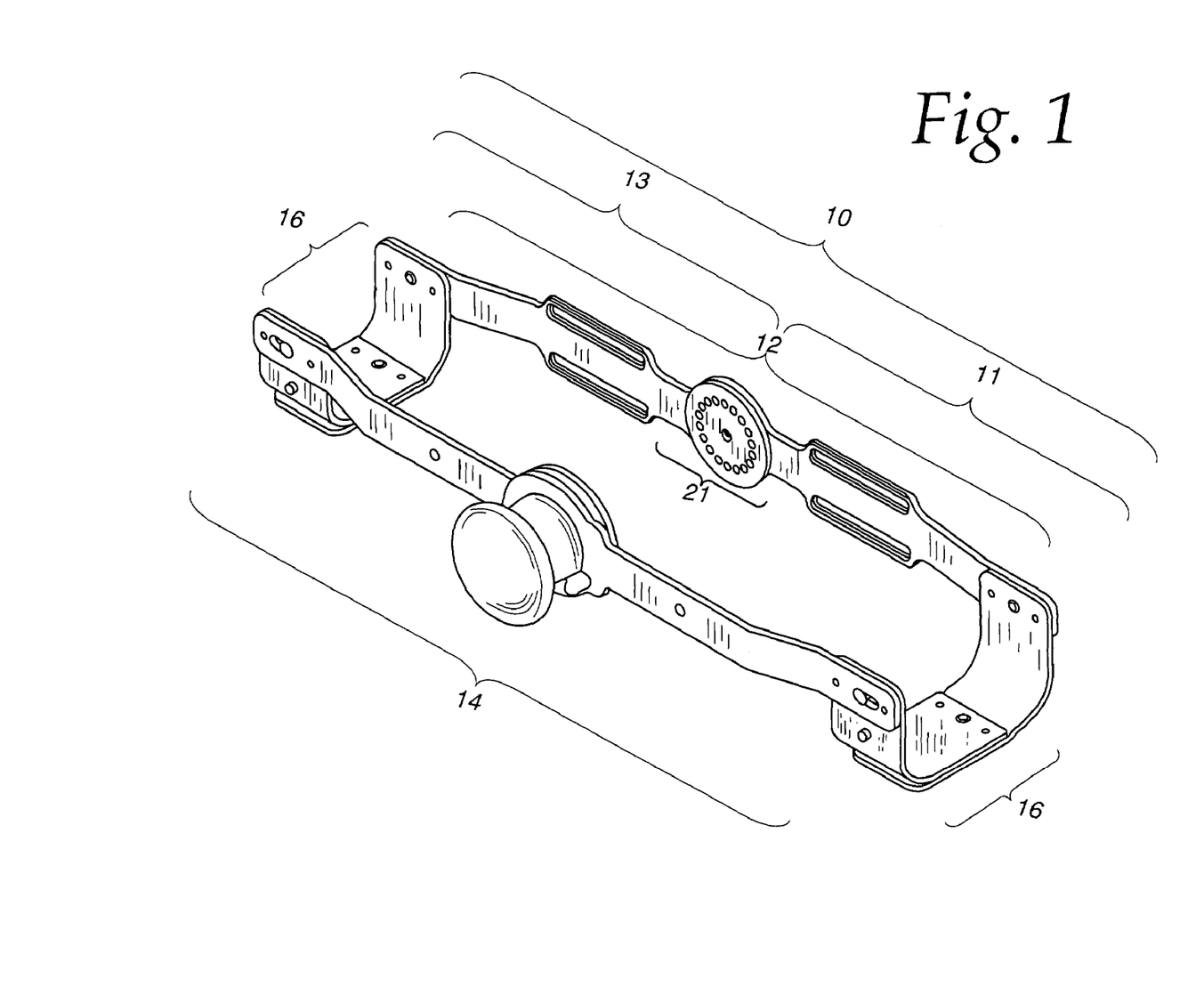
FIG. 1 is an isometric view of one embodiment of the brace in the extended 180° position, with the attachment straps omitted for clarity.

Reference is now made to the figures wherein like parts are referred to by like numerals throughout. With particular reference to FIG. 1, a multi-functional elbow brace 10 according to the present invention comprises a hinged movement arm 12 and a hinged drive arm 14. Adjustable means for connecting hinged movement arm 12 and hinged drive arm 14 comprise adjustable cross brackets 16. Brace 10 comprises a proximal portion 11 and a distal portion 13. In some embodiments, the proximal portions of hinged movement arm 12 and hinged drive arm 14 can be wider than the distal portions thereof.

Figure 2:
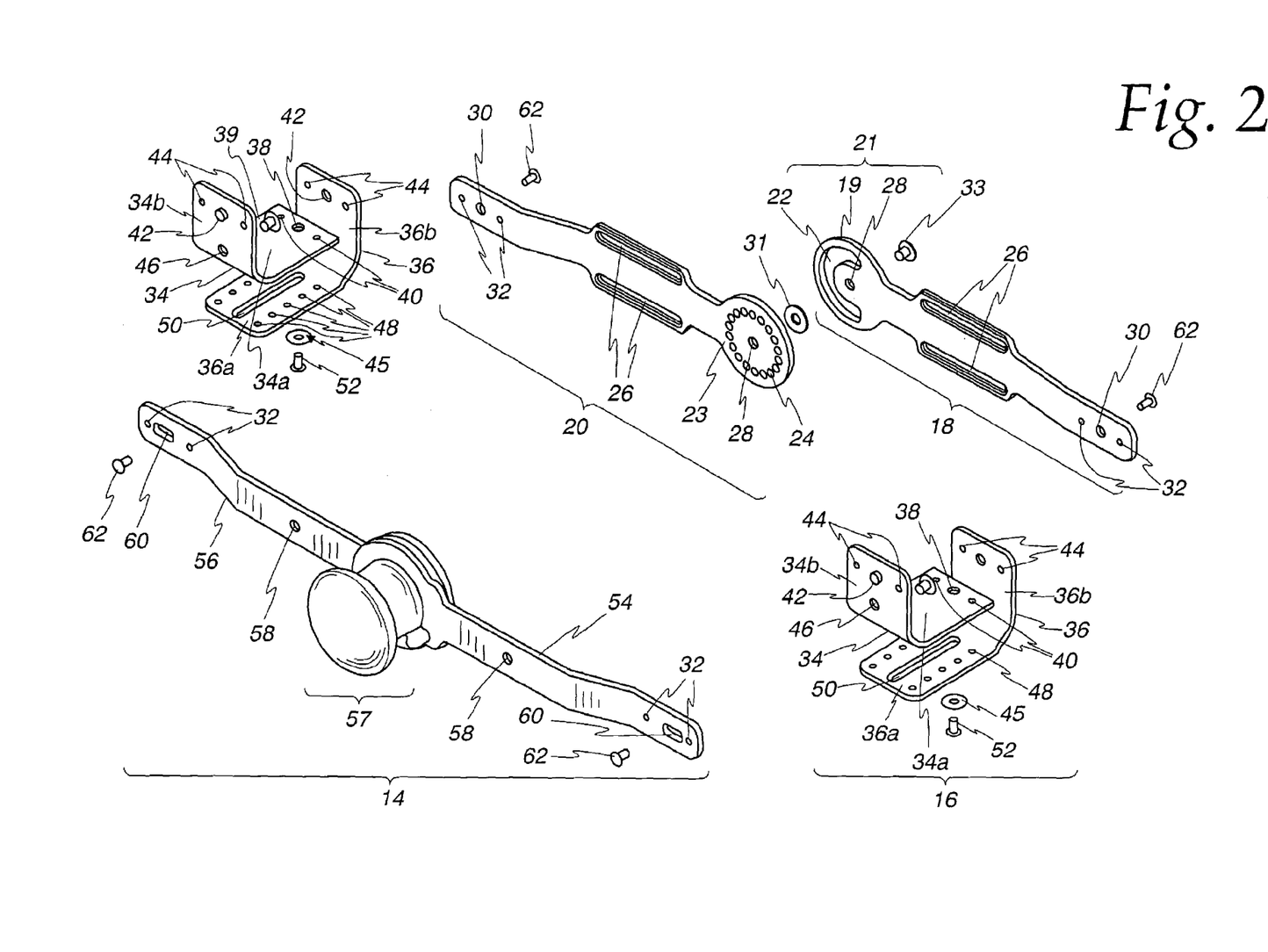
FIG. 2 is a partially exploded isometric view of the brace of FIG. 1.

With reference now to FIG. 2, hinged movement arm 12 comprises a first arm member 18 and a second arm member 20 joined by a means for allowing controlled free movement of the movement arm through a predetermined range of motion; such means can be in the form of range of motion assembly 21. The first arm member 18 comprises radially enlarged end 19 having an arcuate cavity 22 formed therein. The second arm member 20 comprises radially enlarged end 23 having a series of holes 24 formed therein, preferably arranged in a circle or other arcuate configuration. The first and second arm members 18, 20 each comprise two strap slots 26, an axis connection hole 28, a bracket connection hole 30 and two bracket bosses 32 on their inwardly facing surfaces. The bosses 32 can be in the form of small pins that extend through pinholes in the arms, such that the protruding ends of the pins extend from the inner surfaces of the arms. The first arm member 18 is connected to the second arm member 20 by an axial connection means which can comprise means such as a screw, a bolt, or in the illustrated embodiment, an axis rivet 33 in combination with axis washer 31. As may be seen, axis rivet 33 is inserted through the axis connection hole 28 in first arm member 18, through axis washer 31, and into axis connection hole 28 in second arm member 20. Range of motion assembly 21 comprises radially enlarged end 19 of first arm 18, radially enlarged end 23 of second arm 20, their connecting means 33, arcuate cavity 22, holes 24, and one or more range-limiting pins (not shown) that can be inserted through arcuate cavity 22 into one or more of the holes 24. Upon flexion or extension of the user's limb, a range-limiting pin will contact one or another end of arcuate cavity 22, preventing further movement. In the absence of range-limiting pins, there would be unobstructed full rotation between first arm member 18 and second arm member 20. It will be appreciated that, while in the illustrated embodiment the arcuate cavity 22 is in end 19 of first arm 18 and holes 24 are in end 23 of second arm 20, the design could be reversed so that the arcuate cavity is in end 23 of second arm 20 and holes 24 are in end 19 of first arm 18.

Adjustable means for connecting movement arm 12 and drive arm 14 can comprise proximal and distal adjustable brackets 16. In the illustrated embodiment, each adjustable bracket 16 comprises a fixed inner L-shaped flange member 34 having legs 34a, 34b, and an adjustable outer L-shaped flange member 36 having legs 36a, 36b. Leg 34a of inner flange member 34 comprises an adjustment screw hole 38 and two outwardly extending adjustment bosses 40. Leg 34b of inner flange member 34 comprises a brace connection boss 42 having a threaded interior, two boss acceptor holes 44, and a strap-connector hole 46. The outer flange member 36 preferably comprises ten adjustment-boss acceptor holes 48 and brace-adjustment slot 50 on leg 36a thereof, and a brace connection boss 42 with a threaded interior and two boss acceptor holes 44 on leg 36b thereof.

Inner flange member 34 is adjustably connected to outer flange member 36 by means of brace-adjustment screw 52 that extends through a washer 45, through brace-adjustment slot 50 and then into adjustment screw hole 38 formed in leg 34a of upper flange member 34. The width of the adjustable bracket 16 can be varied by inserting the outwardly extending adjustment bosses 40 of leg 34a into the different adjustment-boss acceptor holes 48 in leg 36a before tightening brace-adjustment screw 52. Thus the width of bracket 16 can be adjusted to fit the diameter of a wearer's limb.

Figure 3:
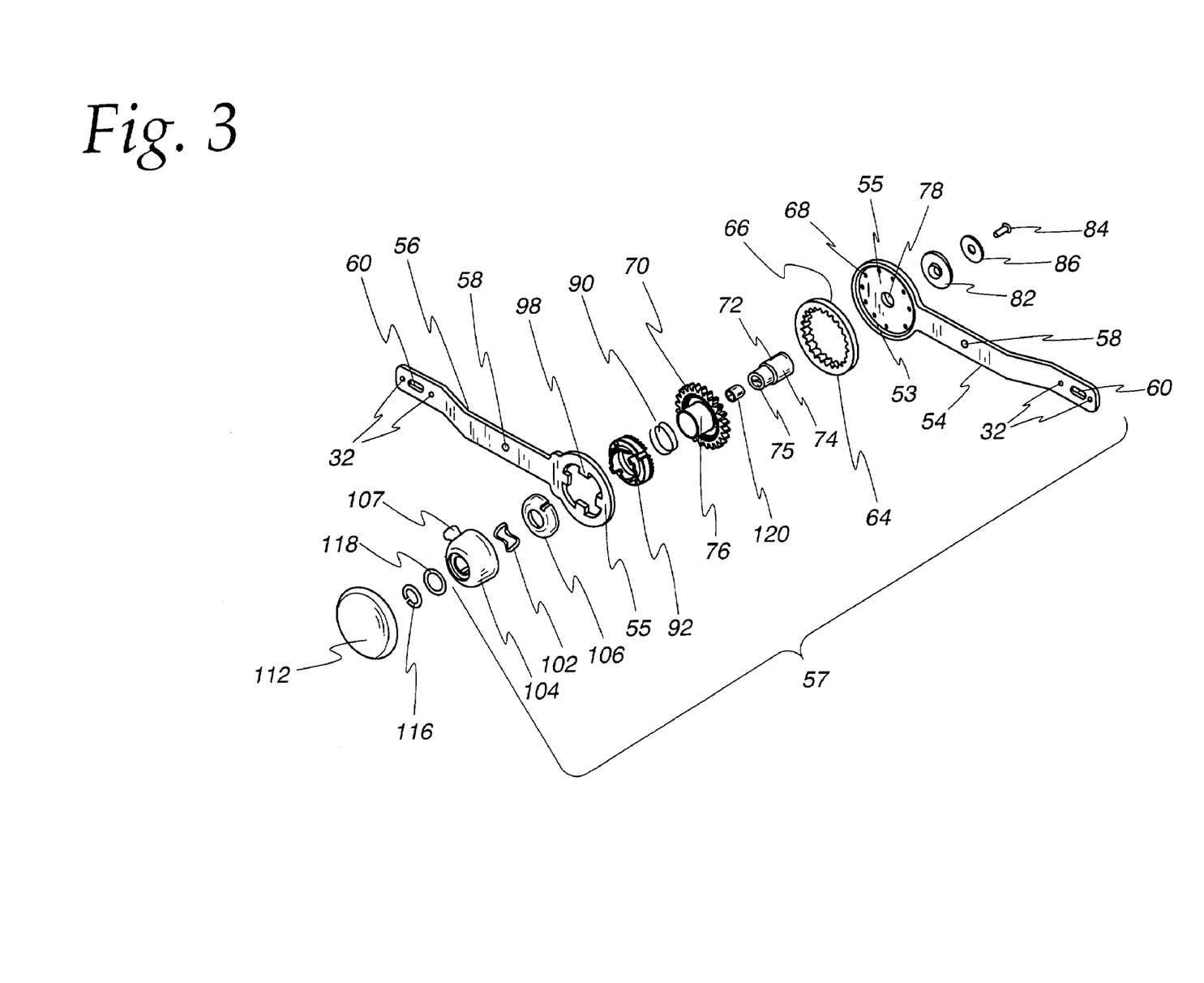
FIG. 3 is an exploded isometric view of the brace drive arm and locking mechanism of FIG. 1.
Figure 3A:
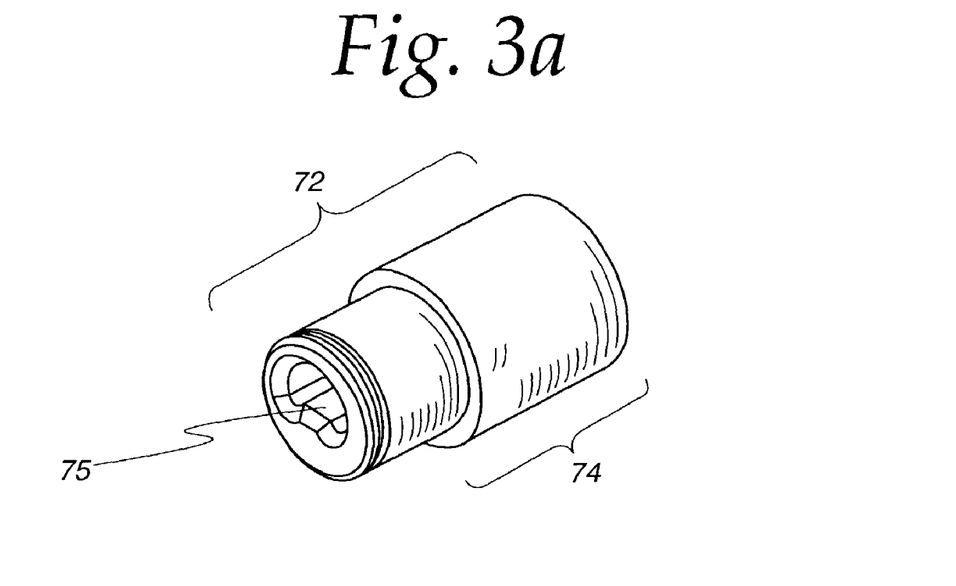
FIG. 3a is an isometric view of the cam shaft of the locking mechanism of FIG. 3.

Hinged drive arm 14 (FIG. 2) comprises third arm member 54 and fourth arm member 56, pivotably joined by a means for releasably locking said hinged drive arm at a predetermined angle; such releasable locking means can be in the form of locking mechanism 57. As shown in FIG. 3, third arm member 54 has an enlarged circular recessed section 53 at one end. Fourth arm member 56 has an enlarged circular section 55 at one end. Both the third and fourth arm members 54, 56 comprise arm strap connection holes 58, a bracket connection slot 60, and two bracket bosses 32. When third and fourth arm members 54, 56 are assembled together as drive arm 14, circular sections 53 and 55 form part of locking mechanism 57, described in detail below.

Adjustable brackets 16 connect the movement arm 12 and drive arm 14. Referring again to FIG. 2, the inner L-shaped flange member 34 of each adjustable bracket 16 is mounted to the drive arm 14 by inserting brace connection boss 42 on bracket leg 34b into the bracket connection slot 60, and inserting the bracket bosses 32 on the third and fourth arms of drive arm 20 into the boss acceptor holes 44. Bracket connection screw 62 is inserted through the bracket connection slot 60 and into the threaded interior of the brace connection boss 42. The outer flange member 36 of the adjustable bracket 16 is mounted to the movement arm 12 by inserting the brace connection boss 42 into the bracket connection hole 30, and inserting the bracket bosses 32 into the boss acceptor holes 44. The bracket connection screw 62 is inserted through the bracket connection hole 30 and into the threaded interior of the brace connection boss 42. It may be seen that the assembled brace 10 can be applied to a user on either the right or left limb, and with the locking mechanism on either the medial or lateral side of the limb. In particular, before the brace is applied to the user the adjustable brackets 16 can be rotated 180 so that the brackets 16 face downward rather than upward as viewed in FIG. 2. The brace 10 then can be turned over and applied to the opposite limb of the user with the proximal portion 11 thereof still proximal to the user, and the distal portion 13 thereof still distal to the user, and with the locking mechanism 57 disposed away from the user's body. In this way, the same brace can be applied to either a left or a right limb, and with the locking mechanism on either the medial side or the lateral side of either limb, at the user's preference.

Figure 3B:
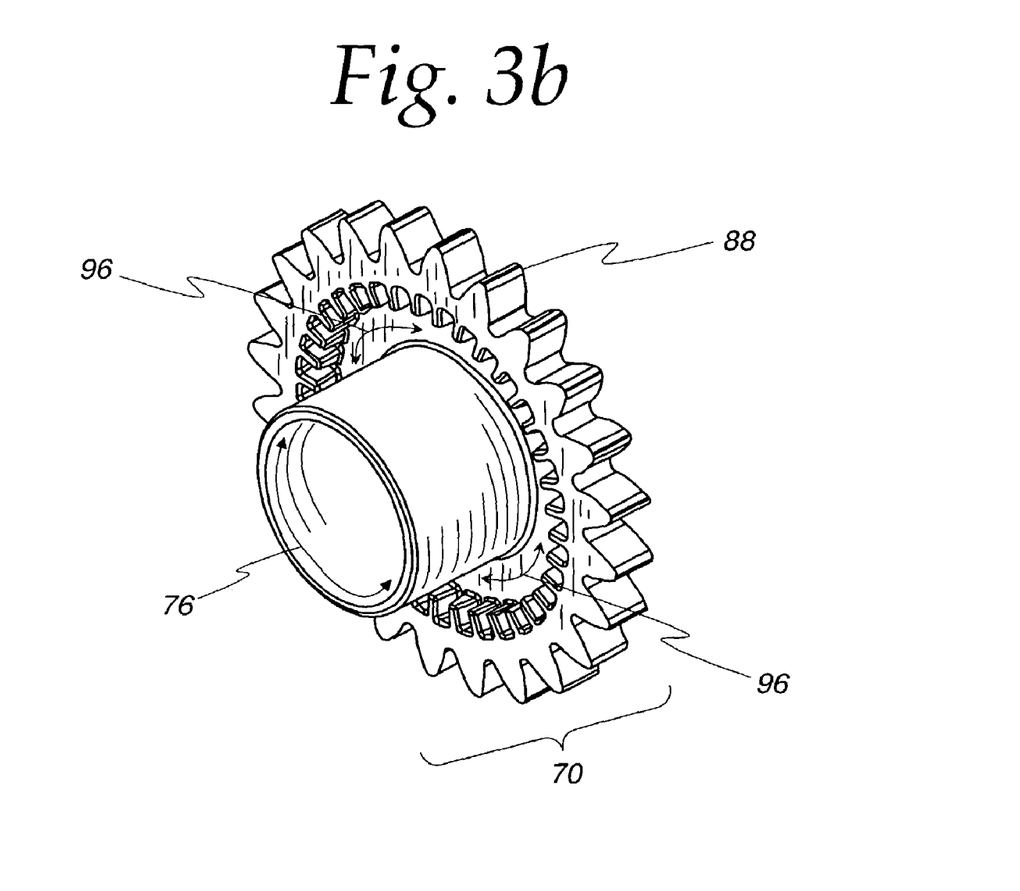
FIG. 3b is an isometric view of the external tooth gear of the locking mechanism of FIG. 3.
Figure 3C:
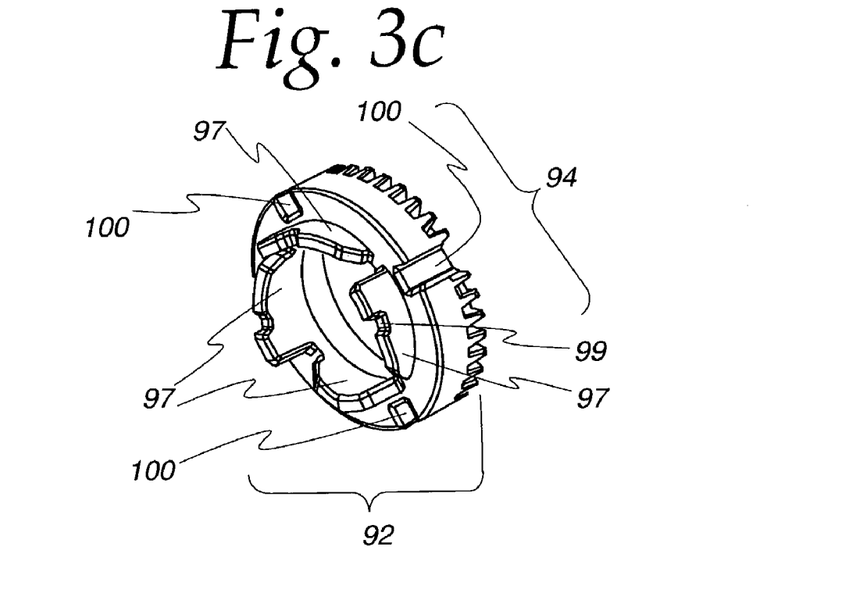
FIG. 3c is an isometric view of the spline plate member of the locking mechanism of FIG. 3.
Figure 3D:
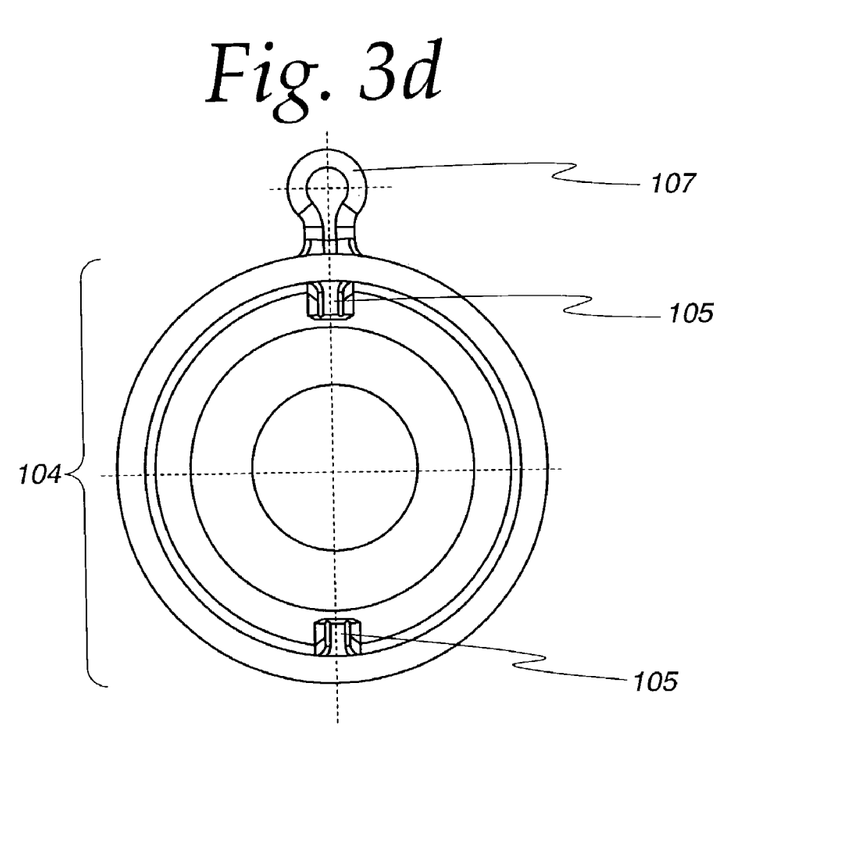
FIG. 3d is a rear view of the concave side of the thumb lever of the locking mechanism of FIG. 3.
Figure 3E:
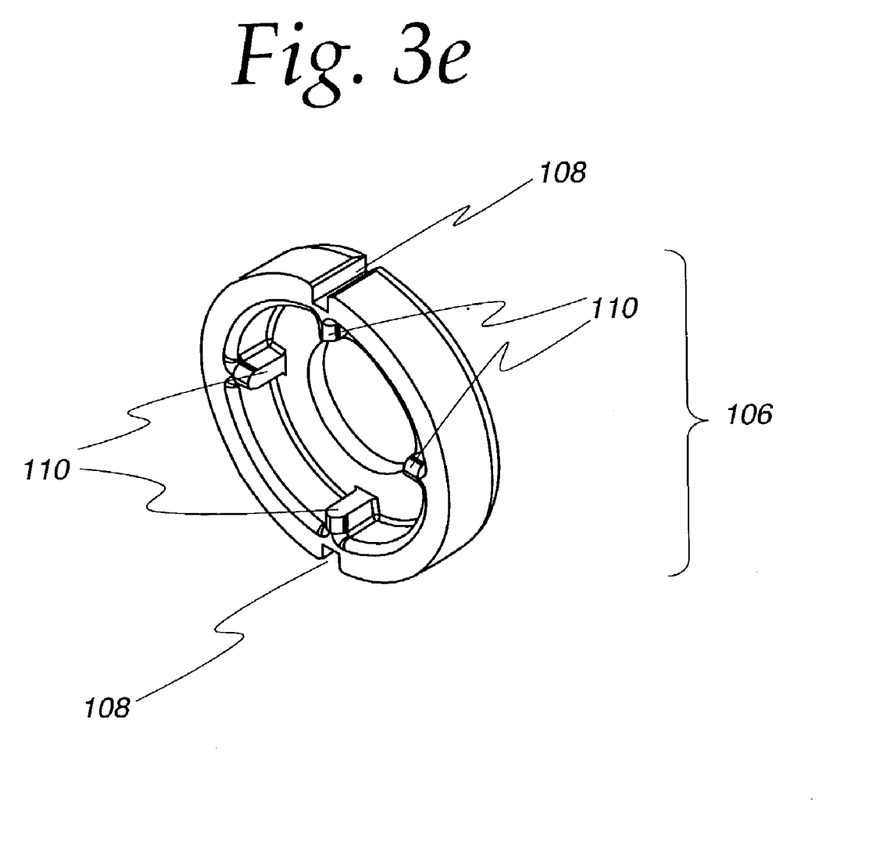
FIG. 3e is an isometric view of the concave side of the joint/spline interface member of the locking mechanism of FIG. 3.
Figure 3F:
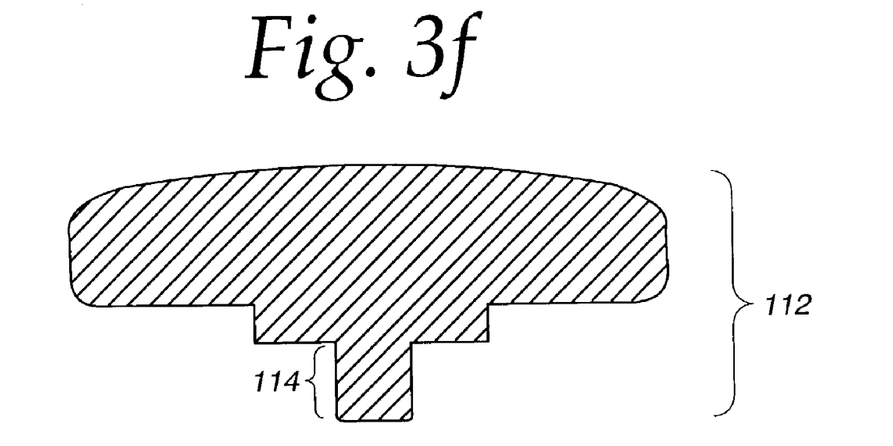
FIG. 3f is a cross-sectional view of one embodiment of a knob of the locking mechanism of FIG. 3.
Figure 3G:
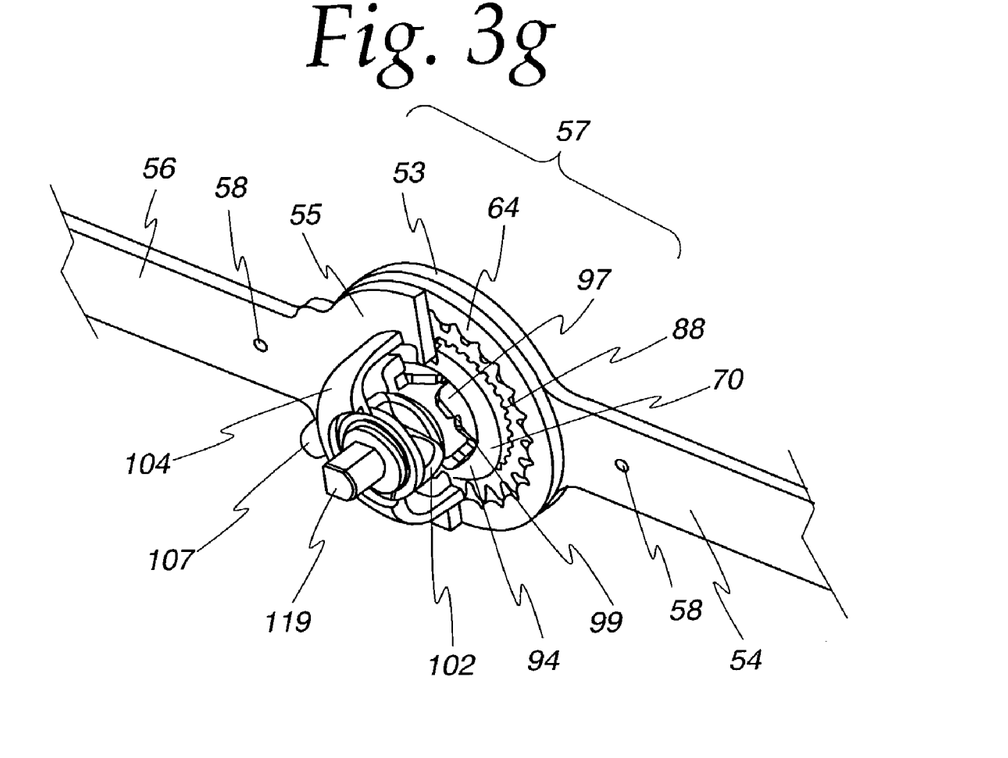
FIG. 3g is an isometric partially cut away view of the locking mechanism in the locked
Figure 3H:
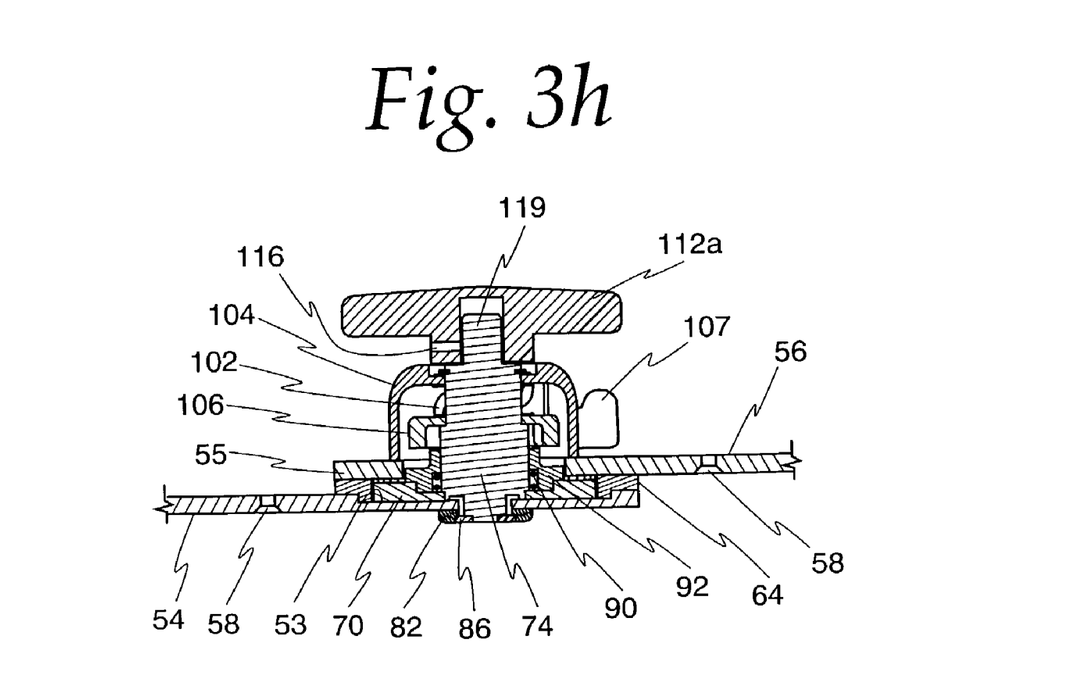
FIG. 3h is a cross-sectional view of the locking mechanism in the locked position.
Figure 3I:
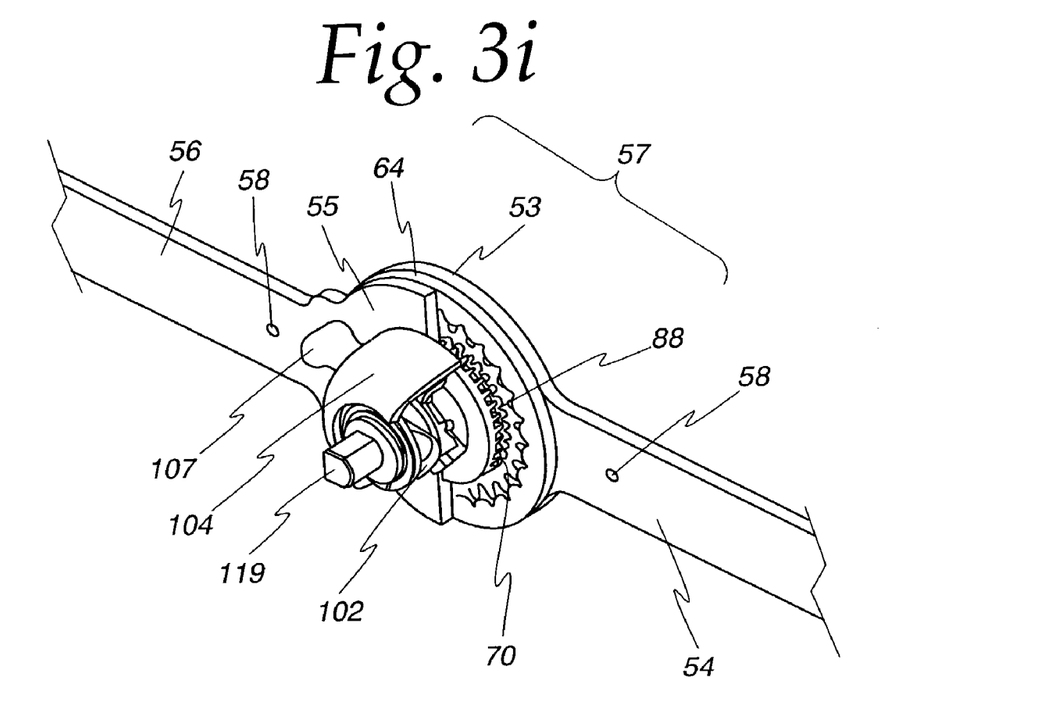
FIG. 3i is an isometric partially cut away view of the locking mechanism in the unlocked position.
Figure 3J:
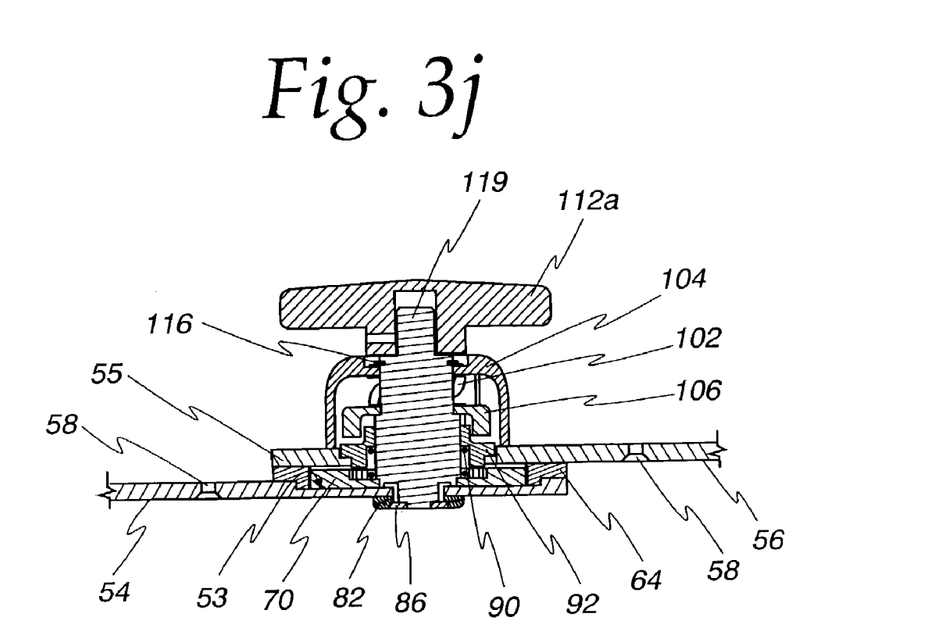
FIG. 3j is a cross-sectional view of the locking mechanism in the unlocked position.

With reference now to FIGS. 3 and 3a–j, the locking mechanism 57 is located at the rotational axis between third arm member 54 and fourth arm member 56. An internal tooth gear 64 has bosses 66 on one side near its perimeter, which bosses engage internal-tooth gear boss acceptor holes 68 located on the inside of recessed circular section 53 of third arm member 54. With reference now to FIG. 3b, an external tooth gear 70 comprises external teeth 88, an internal locking gear 96, and an axial tubular portion 76 that fits snugly onto larger diameter portion 74 of cam shaft 72, shown in FIG. 3a. With reference to FIGS. 3, 3h, and 3j, the cam shaft boss on the opposite end of larger diameter portion 74 of cam shaft 72 is received in axis hole 78 of third arm member 54 and into a shoulder bearing 82. Screw 84 is inserted through washer 86 and the shoulder bearing 82 and into a threaded opening in the cam shaft boss. The external teeth 88 on the external tooth gear 70 fit inside of the internal tooth gear 64 forming a wobble gear. Only some of the external teeth 88 engage the teeth of internal tooth gear 64 at any one time. The wobble gear ratio can be in the range of about 20:1 to about 30:1. In one preferred embodiment, the joining of the internal tooth gear 64 and the external tooth gear 70 creates a wobble gear with a 24:1 ratio. Thus, rotating the external tooth gear 70 twenty-four times causes the internal tooth gear 64 to rotate a full 360°.

Axial tubular portion 76 of external tooth gear 70 fits within a gear member in the form of an annular spline plate member 92, with coil spring 90 disposed therebetween. With reference now to FIG. 3c, the annular spline plate member 92 comprises spline plate axially protruding teeth 94 which face the internal locking gear 96 of the external tooth gear 70. Coil spring 90 biases the annular spline plate member 92 away from external tooth gear 70 so that the spline plate extruding teeth 94 do not engage the internal locking gear 96 of external tooth gear 70 unless a counter-pressure is applied. The annular spline plate member 92 comprises four ramped cam surfaces 97 opposite the spline plate protruding teeth 94, each ramped cam surface 97 comprising a ramp-locking groove 99. The spline plate member 92 further comprises four axially directed slots 100 around its perimeter. Circular end 55 of fourth arm member 56 has a substantially circular orifice with four axially extending tabs 98 along the perimeter. The spline plate member 92 engages fourth arm member 56 by means of the four axially extending tabs 98 that fit into the four axially directed spline plate slots 100. The cam shaft 72, including the clip recess 75 therein, extends through external tooth gear 70, through the center of annular spline plate 92, and through the orifice in circular end 55 of fourth arm member 56.

With reference now to FIG. 3d and FIG. 3e, a concave annular thumb lever 104 comprises two diametrically opposed interface-gripping tabs 105 on its -inner circumference and a thumb knob 107 on its outer circumference. A concave annular lever/spline interface member 106 shown in FIG. 3e comprises two axial grooves 108 diametrically opposed on its outer circumference, and four ramp-engaging tabs 110 on its inner circumference. (It is pointed out that in FIG. 3e the interface member 106 is shown in an orientation opposite that shown in FIG. 3, so that the structure within the concave surface is more readily understood by the viewer.) An override means is provided, the override means being shown in the illustrated embodiment as wave spring 102. Wave spring 102 may be inserted into the inner circumference of the thumb lever 104. The lever/spline interface member 106 is inserted into the inner circumference of the thumb lever 104 so that the wave spring 102 is between the thumb lever 104 and the lever/spline interface member 106.

The exterior grooves 108 on the lever/spline interface member 106 receive the interface-gripping tabs 105 on the inner circumference of thumb lever 104. Both the thumb lever 104 and the lever/spline interface member 106 are oriented with their concave inner surfaces facing the external tooth gear 70. The annular edge of thumb lever 104 is in contact with circular end 55 of fourth arm member 56. The annular edge of the lever/spline interface member 106 engages the ramped cam surfaces 97 of the spline plate member 92. The wearer can push the thumb knob 107 to rotate the thumb lever 104 between a locked and an unlocked position, as described more fully below.

The angle between the third arm member 54 and the fourth arm member 56 of drive arm 14 and the corresponding angle between the first arm member 18 and the second arm member 20 of movement arm 12 can be locked by engaging the locking mechanism 57. The locking mechanism 57 is operated by engaging the thumb knob 107 to rotate thumb lever 104. Because the interface gripping tabs 105 on the interior of thumb lever 104 are received in exterior grooves 108 on interface member 106, rotating the thumb lever 104 by means of thumb knob 107 also rotates the lever/spline interface member 106. As lever/spline interface member 106 rotates, the ramp-engaging tabs 110 on the inner surface thereof move along the ramped cam surfaces 97 located on the spline plate member 92. The force exerted by the ramp-engaging tabs 110 against the ramped cam surfaces 97 urges the spline plate member 92 toward the external tooth gear 70. The force exerted by the ramp-engaging tabs 110 overcomes the counter-force exerted by the coil spring 90 until the spline plate protruding teeth 94 engage the internal locking gear 96 of external tooth gear 70. When the ramp-engaging tabs 110 move a sufficient distance along the ramped cam surfaces 97, the ramp-engaging tabs 110 move against the ramp-locking grooves 99 of spline plate member 92. The counter force exerted by the coil spring 90 against the opposite surface of spline plate member 92 maintains the ramp-locking grooves 99 of spline plate member 92 in engagement with the ramp-engaging tabs 110 of interface 106. When the spline plate protruding teeth 94 engage the internal locking gear 96, the third arm member 54 and the fourth arm member 56 cannot rotate freely around each other, and the angle between the two is fixed. Rotating the thumb lever 104 in the opposite direction disengages the spline plate protruding teeth 94 from the internal locking gear 96, and the third arm member 54 can rotate freely with respect to the fourth arm member 56 about the axis between the two. This occurs because the rotation of the thumb lever 104 rotates the interface 106 which removes the force of the ramp-engaging tabs 110 on the spline plate member 92 as they move along the ramped cam surfaces 97. When the angle between the arms is unlocked, free-range-of-motion therapy, controlled by range of motion assembly 21, can be performed on the wearer's joint, even though the wearer does not remove the brace. When the angle between the arms is locked by operation of thumb lever 104, static stretch therapy can be performed on the wearer's joint in either flexion of extension. The brace can be locked at any angle desired for appropriate stretch therapy, moreover, this angle can be adjusted from time to time as effective therapy requires.

The invention described herein further comprises an angle-adjustment means that allows the static stretch therapy angle to be adjusted even when the locking mechanism 57 is locked. As shown in FIG. 3f, a knob 112 comprises a knob shaft 114. As shown in FIG. 3, the knob shaft 114 is inserted through retaining ring 116, washer 118, annular thumb lever 104, wave spring 102 and annular lever/spline interface member 106, and inserted into a knob connection means operatively coupled to cam shaft 72. In the illustrated embodiment, knob connection means is in the form of clip 120.

When the locking mechanism 57 is in the locked position, the fixed angle between the third arm member 54 and the fourth arm member 56 can be changed by rotating the knob 112 in the desired direction. Because the knob 112 is operatively connected to the cam shaft 72, rotating the knob 112 rotates the cam shaft 72 in the same direction. The rotation of the cam shaft 72 rotates the external tooth gear 70 as a wobble gear inside the internal tooth gear 64. In the preferred embodiment, a 24:1 ratio of the external tooth gear 70 to the internal tooth gear 64 requires twenty-four rotations of the knob 112 to rotate the fourth arm member 56 in a 360° arc around the third arm member 54. The adjustment of the angle allows the static stretch of the joint to be increased or decreased in either flexion or extension. In another preferred embodiment, the fourth arm member 56 has a calibrated scale at its circular end 55 and the third arm member 54 has a calibration mark. The scale and mark convey the angle between the fourth arm member 56 and third arm member 54. This scale and mark allow the user to monitor the degree of extension and flexion of the joint.

Once the desired angle of flexion or extension has been selected and the brace has been locked into position, the knob 112 can be removed from the brace 10 for the convenience and comfort of the wearer. The knob 112 is connected to the brace 10 by the knob shaft 114 inserted into the clip 120, which in turn is inserted into the clip recess 75 of the cam shaft 72. The clip 120 is adequate to maintain a connection between the knob shaft 114 and the cam shaft 72 during normal use of the elbow brace. When a force in the direction opposite the cam shaft 72 is applied to the knob 112, the clip 120 no longer maintains the connection between the knob shaft 114 and the cam shaft 72. Removing the knob 112 can create greater comfort and convenience for the wearer. In particular, removing the knob 112 allows the wearer to place thumb lever 104 against the wearer's body without injury from an exposed shaft. The knob 112 easily can be re-attached to the brace by placing the knob shaft 114 into the clip 120 at the clip recess 75 on the cam shaft 72, and applying force toward the cam shaft 72. Other means for easy mechanical detachment and reattachment of the knob will be known to those skilled in the mechanical arts. In the embodiment shown in FIGS. 3h and 3i, the knob 112a does not have a shaft, but instead is received on a protruding shaft 119. While this embodiment performs the exact same function in terms of operating the lock mechanism as described below, removable of the knob 112a may not be as desirable because the exposed connection means 119 does not provide a low-profile surface, and may be troublesome to the wearer.

An override means that prevents damage to the locking mechanism 57 from force applied to the brace while the locking mechanism 57 is in the locked position comprises wave spring 102. The wave spring 102 allows the engaged spline plate protruding teeth 94 to temporarily disengage from the internal locking gear 96 if a significant external force is applied to the elbow brace. The disengagement occurs when the lever/spline interface member 106 moves against the force of the wave spring 102 and into the thumb lever 104, allowing the ramp-engaging tabs 110 to move out of the ramp-locking grooves 99, which allows the coil spring 90 to push the spline plate member 92 away from the external tooth gear 70. This disengagement protects the spline plate protruding teeth 94 and the internal locking gear 96 from breakage in the event a force greater than the failure point of the apparatus is applied.

The range of motion assembly 21 created in part by the cavity 22 and the holes 24 can limit the range of the angles of free movement of the distal portion 13 of the brace relative to the proximal portion 11. This range of angles can be limited by inserting range-limiting pins (not shown) through the cavity 22 and into one or more holes 24. Upon rotation, a range-limiting pin will contact the upper or lower edge of the cavity 22, preventing further rotation. The range of motion assembly 21 can limit the maximum and minimum angle whether the locking mechanism 57 is locked or unlocked. The range of motion assembly 21 also can lock the elbow brace into one angle by appropriate placement of the range-limiting pins.

In the preferred embodiment, straps attach the brace 10 to the wearer. For example, in the embodiment in which the brace is adapted for use on a wearer's arm, there can be four straps located respectively at the wearer's wrist, forearm, bicep, and upper arm. The wearer's bicep and upper arm are placed on the proximal portion 11 of the brace comprising first arm member 18 and third arm member 54, while the wearer's wrist and forearm are placed on the distal portion 13 of the brace comprising the second arm member 20 and the fourth arm member 56. There are two types of straps used in the illustrated embodiment. End straps 122 are used at the ends of the brace, i.e., at the wrist and upper arm locations, where the adjustable cross brackets are located. Slot straps 128 are used at the bicep and forearm portions of the brace.

Figure 4:
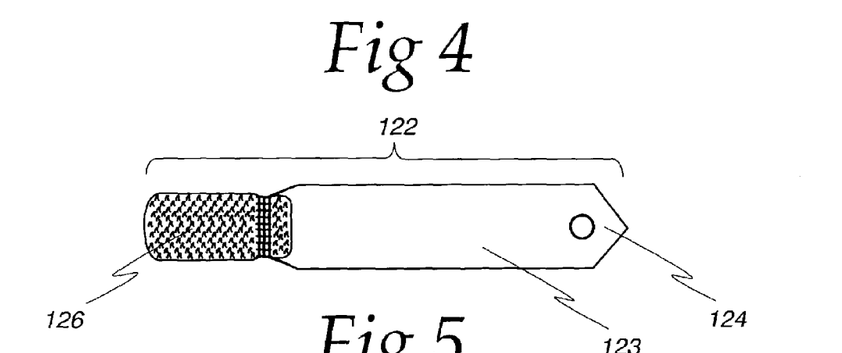
FIG. 4 is a plan view of the end strap used with the brace.

With reference now to FIG. 4, an end strap 122 is provided, comprising a strap reinforcement 124 welded near one end of a strip 123 of loop bearing material having a tab portion 126 of hook bearing material at its opposite end. Referring to FIG. 2, end strap 122 is attached to the third arm member 54 by inserting a rivet, not shown, through strap reinforcement 124 and strap-connector hole 46 in leg 34b of bracket 16. A D-ring, not shown, is affixed to the exterior surface of first arm 18; the bracket connection screw 62 that fits into bracket connection hole 30 of first arm 18 can be used for this purpose. The same means are used to attach a second end strap 122 to the wrist portion of fourth arm 56. Because the adjustable cross brackets 16 extend underneath the wearer's arm at these locations, the end straps 122 need only extend over the top of the wearer's upper arm and wrist, respectively. When the brace 10 is applied to a user, the end straps 122 are looped through the D-rings and the hook bearing tab 126 engages the loop bearing strip 123 so as to secure the brace 10 comfortably to the user.

Figure 6:
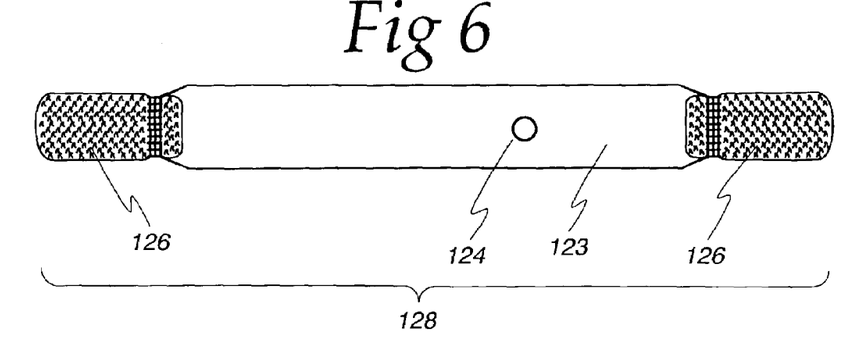
FIG. 6 is a plan view of the slot strap used with the brace of FIG. 1.

With reference now to FIG. 6, an elongated slot strap 128 comprises a strap reinforcement 124 welded somewhat off-center to a strip 123 of loop-bearing material. Hook bearing tabs 126 are on either end of loop bearing strip 123. With reference now to FIG. 2, the slot straps 128 are fastened to third arm member 54 and fourth arm member 56 by a connection means such as a rivet, not shown, that passes through reinforcement 124 and then into arm strap connection hole 58 located on the third arm member 54 and fourth arm member 56. Due to the off-center placement of reinforcement 124, each slot strap 128 will have a longer portion and a shorter portion. Generally, the longer portion of the slot strap 128 will extend over the wearer's bicep while the shorter portion will extend under the wearer's arm. The hook-bearing ends 126 of each slot strap 122 are threaded through strap slots 26 located on the first arm member 18 and second arm member 20, respectively. Each slot strap 128 is folded back upon itself and secured by pressing the hook bearing tab 126 against loop bearing strip 123.

Figure 5:
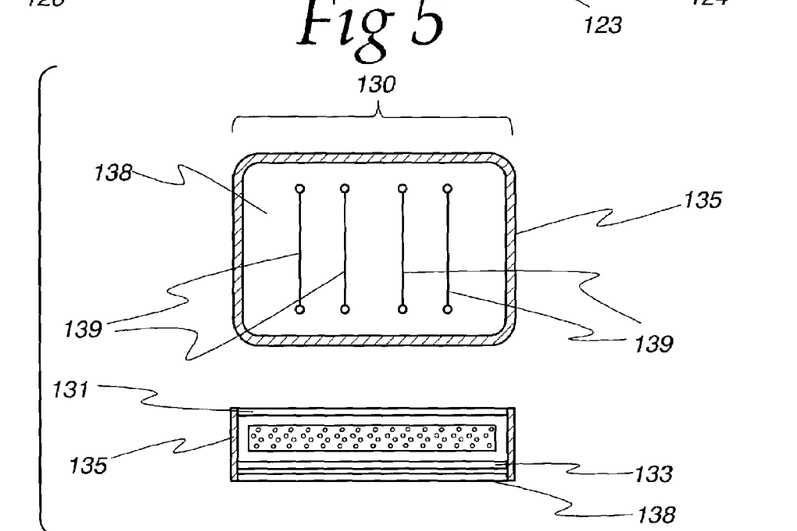
FIG. 5 is a plan view of an air bladder useful with the brace of the present invention.
Figure 7:
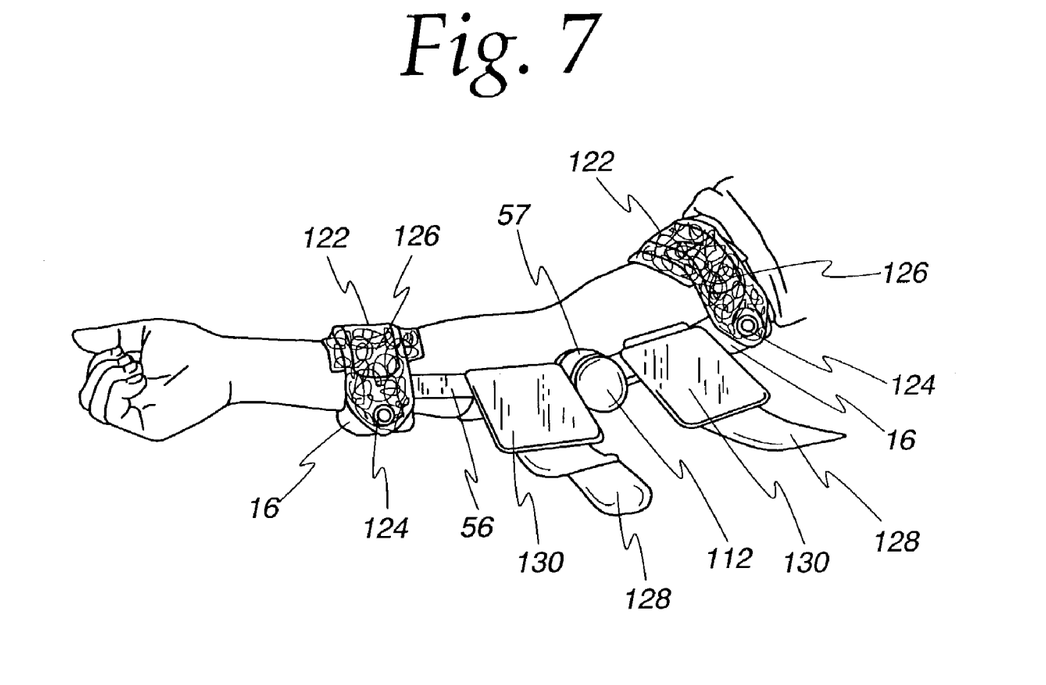
FIG. 7 is a view of an embodiment of the brace of the instant invention being applied to the arm of a wearer with the end straps secured and the slot straps unsecured.
Figure 8:
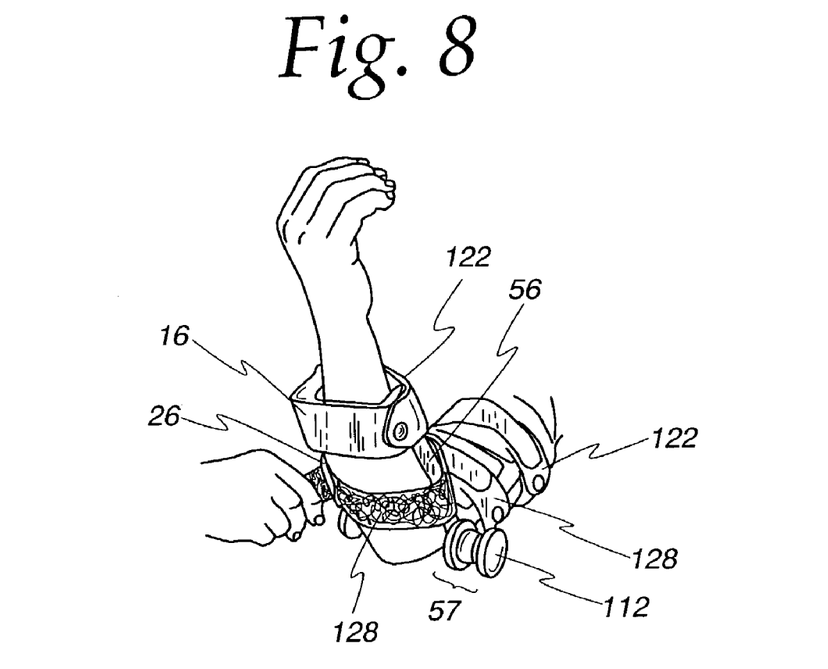
FIG. 8 is a view of the brace of FIG. 7 being positioned on the arm and the slot straps being adjusted to obtain proper brace alignment with the elbow joint of the wearer.

In one preferred embodiment, an aircell or bladder 130 filled with air is connected to the end straps 122 and/or the slot straps 128. With reference now to FIG. 5, a preinflated air bladder 130 comprises two pieces of flexible air-impervious plastic 131, 133 sealed at their perimeters such as with an RF seal 135. Advantageously, the preinflated air bladder can have a piece of soft foam 137 between plastic 131, 133 for ease of manufacture, to maintain the inflation of the bladder, and to further promote the user's comfort. A fabric covering 138 over at least one of the plastic pieces 133 is provide with slits 139 for receiving straps 122 or 128 in belt-loop fashion. The use of such air bladders is illustrated in FIGS. 7 and 8. The air bladder 130 helps increase the wearer's comfort and helps secure the brace to the wearer's limb by distributing the load of the strap.

While this invention has been described in connection with a preferred embodiment, it is clearly to be understood that this is done only by way of example and not as a limitation to the scope of our invention as set forth in the objects thereof and in the appended claims. For example, it will be appreciated that the disclosed brace can be modified for use with a knee or other joint.

We claim:

1. A joint brace for providing therapy to an injured joint, such joint brace comprising
    (a) a hinged movement arm;
    (b) means at said movement arm hinge for allowing controlled free movement through the movement arm hinge about a predetermined range of motion;
    (c) a hinged drive arm;
    (d) means at said drive arm hinge for releasably locking said drive arm hinge at a predetermined angle;
    (e) means for adjusting the hinge angle of said drive arm, said adjusting means being operable when said releasable locking means is in a locked configuration; and
    (f) adjustable means for connecting said movement arm to said drive arm such that the hinges thereof are in alignment.

2. The joint brace of claim 1 wherein said releasable locking means comprises a first gear member, a second gear member, and a lever means operable on said first gear member to cause said first gear member to be engaged or disengaged from said second gear member, whereby when said first gear member is engaged with said second gear member said hinged drive arm is locked, and when said first gear member is not engaged with said gear member said hinged drive arm is unlocked.

3. The joint brace of claim 2 wherein said first gear member further comprises at least one cam surface by which the movement of said lever means is transmitted to cause said first gear member to engage and disengage from said second gear member.

4. The joint brace of claim 3 further comprising an interface member that operatively couples said lever means to said at least one cam surface of said first gear member.

5. The joint brace of claim 4 further comprising an override means disposed between said lever means and said interface member.

6. The joint brace of claim 3 wherein said hinged drive arm comprises a first drive arm member and a second drive arm member in hinged engagement, said second gear member being operatively coupled to one of said drive arm members and said first gear member being operatively coupled to the other drive arm member, such that engagement of said first and second gear members serves to lock said first and second drive arm members with respect to one another.

7. The joint brace of claim 1 wherein said drive arm comprises a first drive arm member and a second drive arm member in hinged engagement, said adjusting means comprising a rotatable knob operatively coupled to one of said drive arm members, such that rotation of said knob causes rotation of said one drive arm member about said drive arm hinge.

8. The joint brace of claim 7 wherein said rotatable knob is operatively coupled to said one drive arm member by means of a wobble gear.

9. The joint brace of claim 8 wherein said wobble gear comprises an external tooth gear and an internal tooth gear and ratio of the external tooth gear to the internal tooth gear is in the range of about 20:1 to about 30:1.

10. The joint brace of claim 9 wherein said wobble gear ratio is 24:1.

11. The joint brace of claim 7 wherein said rotatable knob is removable.

12. The joint brace of claim 1 wherein said hinged movement arm comprises a first movement arm member and a second movement arm member in hinged engagement, and said means for allowing controlled free movement through the movement arm hinge comprises means for limiting rotation of said first and second movement arm members with respect to one another about said movement arm hinge.

13. The joint brace of claim 12 wherein said means for limiting rotation comprises an arcuate cavity on one of said movement arm members, said arcuate cavity having two ends, at least one hole on said other movement arm member, said hole being alignable with an area of said arcuate cavity, and at least one pin member extendable through said at least one hole and said arcuate cavity, such that rotation of said first and second movement arm members with respect to one another will cause said pin member to engage one or the other end of said arcuate cavity, thereby limiting said rotation of said first and second arm members with respect to one another.

14. The joint brace of claim 1 further comprising at least one strap for securing said brace to a wearer.

15. The joint brace of claim 14 wherein a pre-inflated bladder is disposed between said at least one strap and a wearer.

16. The joint brace of claim 14 wherein said strap comprises a portion of hook-bearing material and a portion of loop bearing material.

17. The joint brace of claim 14 wherein said strap is operatively mounted to said drive arm and said movement arm is provided with means for receiving said strap therethrough.

18. The joint brace of claim 1 wherein said adjustable connection means comprises a first member coupled to said drive arm and a second member coupled to said movement arm, said first and second adjustable connection means members being engageable with one another at more than one location therein, whereby the width of the adjustable connection means can be varied.

19. The joint brace of claim 18 wherein said adjustable connection means can be rotated 180° with respect to said drive arm and said movement arm, whereby said joint brace can be adapted for use on either a right or left limb of a user.

20. A joint brace for providing therapy to an injured joint, such joint brace comprising
    a movement arm having a first hinge;
    an assembly at the first hinge adapted to control movement of the movement arm about the first hinge;
    a drive arm having a second hinge;
    a locking mechanism at the second hinge adapted to releasably lock the second hinge at an angle;
    a member adapted to adjust the hinge angle of the drive arm while the locking mechanism is in a locked configuration; and
    an adjustable bracket for connecting the movement arm to the drive arm such that the first and second hinges are in alignment.

21. The joint brace of claim 20, wherein the locking mechanism comprises a first gear member, a second gear member, and a lever operable on the first gear member to engage the first gear member with the second gear member.

22. The joint brace of claim 21, wherein the first gear member engages the second gear member to lock the second hinge at an angle.

23. The joint brace of claim 20 wherein the drive arm comprises a first drive arm member and a second drive arm member in hinged engagement.

24. The joint brace of claim 20, wherein the movement arm comprises a first movement arm member and a second movement arm member in hinged engagement, and
    the assembly for controlling movement of the movement arm comprises
        an arcuate cavity on the first movement arm member, the arcuate cavity having a first end and a second end,
        a first hole on the second movement arm member, the first hole being alignable with the arcuate cavity, and
        at least one pin member extendable through the first hole and the arcuate cavity, such that rotation of the first and second movement arm members with respect to one another will cause the pin member to engage the first or second end of the arcuate cavity.

25. The joint brace of claim 20, further comprising a pre-inflated bladder disposed on a strap for securing the brace to a wearer.

26. The joint brace of claim 20, wherein the adjustable bracket comprises a first member coupled to the drive arm and a second member coupled to the movement arm, the first member engageable with the second member at a first or a second location.

27. The joint brace of claim 20, wherein the member comprises a rotatable knob operatively coupled to a drive arm member.

28. The joint brace of claim 27, wherein the rotatable knob is adapted such that rotation of the knob causes rotation of the drive arm member about the second hinge.

29. The joint brace of claim 27 wherein the rotatable knob is operatively coupled to at least one of the first and second drive arm members by a gear member.

30. The joint brace of claim 29, wherein the gear member is a wobble gear.

* * * * *